United States Patent
Ein-Gal

(10) Patent No.: US 7,942,872 B2
(45) Date of Patent: May 17, 2011

(54) BLENDED MONOPOLAR AND BIPOLAR APPLICATION OF RF ENERGY

(76) Inventor: Moshe Ein-Gal, Ramat Hasharon (IL)

( * ) Notice: Subject to any disclaimer, the term of this patent is extended or adjusted under 35 U.S.C. 154(b) by 1433 days.

(21) Appl. No.: 11/362,066

(22) Filed: Feb. 27, 2006

(65) Prior Publication Data

US 2007/0203482 A1    Aug. 30, 2007

(51) Int. Cl.
*A61B 18/10* (2006.01)
(52) U.S. Cl. ............................. 606/34; 606/41
(58) Field of Classification Search ............ 606/32–52
See application file for complete search history.

(56) References Cited

U.S. PATENT DOCUMENTS

| | | | | |
|---|---|---|---|---|
| 5,269,304 | A * | 12/1993 | Matthews | 607/46 |
| 5,383,917 | A * | 1/1995 | Desai et al. | 607/102 |
| 5,542,916 | A * | 8/1996 | Hirsch et al. | 604/22 |
| 5,697,928 | A * | 12/1997 | Walcott et al. | 606/41 |
| 5,837,001 | A * | 11/1998 | Mackey | 607/102 |
| 5,931,835 | A * | 8/1999 | Mackey | 606/34 |
| 6,049,737 | A * | 4/2000 | Simpson et al. | 607/119 |
| 6,139,546 | A * | 10/2000 | Koenig et al. | 606/34 |
| 6,200,314 | B1 * | 3/2001 | Sherman | 606/34 |
| 6,309,386 | B1 * | 10/2001 | Bek | 606/34 |
| 6,416,509 | B1 * | 7/2002 | Goble et al. | 606/37 |
| 6,635,056 | B2 * | 10/2003 | Kadhiresan et al. | 606/34 |
| 6,730,078 | B2 * | 5/2004 | Simpson et al. | 606/34 |
| 7,357,800 | B2 * | 4/2008 | Swanson | 606/39 |
| 7,520,877 | B2 * | 4/2009 | Lee et al. | 606/42 |
| 2007/0282322 | A1 * | 12/2007 | Dabney et al. | 606/39 |

* cited by examiner

*Primary Examiner* — Michael Peffley
*Assistant Examiner* — Ronald Hupczey, Jr.
(74) *Attorney, Agent, or Firm* — Dekel Patent Ltd.; David Klein

(57) ABSTRACT

A system including at least two target electrodes and at least one return electrode, at least two RF power sources in electrical communication with the electrodes and operative to generate RF energy waveforms to the at least two target electrodes, one of the at least two target electrodes cooperating with the at least one return electrode to define a monopolar RF energy delivery channel and another of the at least two target electrodes cooperating with the at least one return electrode to define another monopolar RF energy delivery channel, the at least one return electrode being common to both channels, wherein the at least two target electrodes being operable in a bipolar mode of RF energy delivery, and a waveform manipulator operable to control and manipulate the waveforms to the at least two target electrodes so as to selectively provide pure monopolar, pure bipolar and a blend of monopolar and bipolar modes of RF energy delivery.

5 Claims, 2 Drawing Sheets

BLENDED MONOPOLAR AND BIPOLAR APPLICATION OF RF ENERGY

FIELD OF THE INVENTION

The present invention relates generally to electrosurgical apparatus for tissue ablation generally, and particularly to apparatus for radio frequency (RF) tissue ablation.

BACKGROUND OF THE INVENTION

Radio frequency (RF) tissue ablation is a well-known technique, e.g., in electrosurgery and thermal therapy, for making thermal lesions in the vicinity of an uninsulated tip of an electrode due to tissue coagulation caused by resistive heating. Voltage applied to electrodes causes electrical current flow through tissue and heat production due to tissue electrical resistance (Joule heating). The electrode can be applied directly on superficial structures, surgically, endoscopically, laparascopically, or even via a transcatheter access such as a treatment for symptomatic cardiac arrhythmias. If the electrode is formed as a needle, then the electrode may be inserted interstitially, and guided by imaging.

In a monopolar mode, current flows between a small target electrode and a large counter-electrode placed further away from the target. Due to the difference in the sizes of the electrodes, current density and associated Joule heat production are much higher at the target than at the return electrode. In contrast, in a bipolar mode, high density current flows between two adjacent target electrodes. Joule heat production is confined to a small volume due to electrodes size and proximity.

Thermal treatment amounts to applying high density current for a sufficient time to cause elevated temperature and associated physiological changes, e.g., coagulation, at a volume of tissue. Monopolar current flows through a larger volume compared to bipolar current. Consequently, monopolar Joule heating has a deeper penetration compared to bipolar heating, where the heat is confined to a small volume at the target electrodes Electrosurgical apparatus is known that provides an option of selecting and switching between pure monopolar mode and pure bipolar mode. For example, U.S. Pat. No. 6,837,884 to Woloszko describes electrosurgical apparatus and methods for ablating, coagulating, shrinking, stiffening, or other treatment of a target tissue of a patient. The apparatus includes an electrosurgical probe, and an introducer needle adapted for passing through the distal end of the probe. In some embodiments, the electrosurgical system may include a dispersive return electrode for switching between bipolar and monopolar modes.

SUMMARY OF THE INVENTION

The present invention seeks to provide a novel system for application of RF energy that blends monopolar and bipolar modes of operation, as is described more in detail hereinbelow. This is different from the known prior art that is only capable of switching between a pure monopolar mode and a pure bipolar mode. The blended combination of monopolar and bipolar modes of operation may provide synergistic effects heretofore unknown in the prior art.

There is provided in accordance with an embodiment of the present invention a system including at least two target electrodes and at least one return electrode, at least two RF power sources in electrical communication with the electrodes and operative to generate RF energy waveforms to the at least two target electrodes, one of the at least two target electrodes cooperating with the at least one return electrode to define a monopolar RF energy delivery channel and another of the at least two target electrodes cooperating with the at least one return electrode to define another monopolar RF energy delivery channel, the at least one return electrode being common to both channels, wherein the at least two target electrodes being operable in a bipolar mode of RF energy delivery, and a waveform manipulator operable to control and manipulate the waveforms to the at least two target electrodes so as to selectively provide pure monopolar, pure bipolar and a blend of monopolar and bipolar modes of RF energy delivery.

The distance between the at least two target electrodes may be smaller than a spacing between the at least two target electrodes and the common return electrode. The waveforms may be sinusoidal with identical frequency, and the waveform manipulator may modify an inter-waveforms phase. Alternatively, the waveforms may be sinusoidal with respective frequencies separated by a beat frequency, and the waveform manipulator may modulate the waveforms according to a phase of the beat frequency. Alternatively, the waveforms may be similar and have opposite polarities, wherein the ratio of amplitudes of the waveforms is controlled. Alternatively, the waveforms may be identical, and the waveform manipulator may delay one waveform relative to another.

DETAILED DESCRIPTION OF EMBODIMENTS

Figure 1:
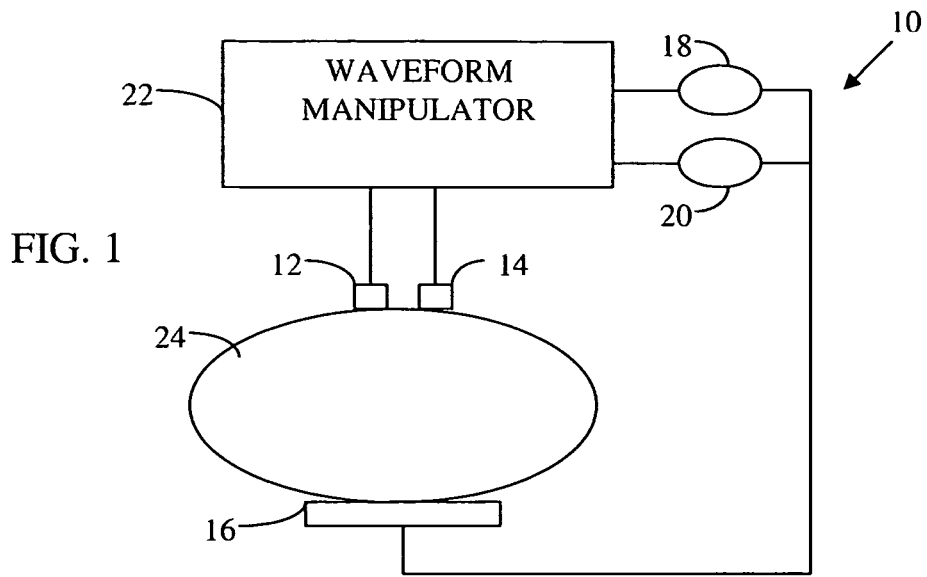
FIG. 1 is a simplified pictorial illustration of a system for blending monopolar and bipolar modes of RF energy delivery, constructed and operative in accordance with an embodiment of the present invention.

Reference is made to FIG. 1, which illustrates a system 10 for blending monopolar and bipolar modes of RF energy delivery, constructed and operative in accordance with an embodiment of the present invention.

System 10 may include two or more target electrodes 12 and 14 (two are shown in the non-limiting illustrated embodiment) and one or more return electrodes 16 (one is shown in the non-limiting illustrated embodiment). RF power sources 18 and 20 may energize the electrodes 12, 14 and 16, in a manner described below, by generating RF energy waveforms (e.g., voltage or current waveforms) to the electrodes. A waveform manipulator 22 may control and manipulate the waveforms to the electrodes so as to blend monopolar and bipolar modes of energy as described below. The waveform manipulator 22 may include any known device for varying operative characteristics of the RF energy generated by the RF power sources, such as but not limited to, frequency, phase and amplitude. In such a manner, system 10 is capable of selectively combining monopolar and bipolar modes to better control the current distribution in a target 24 (e.g., tissue in a human body or non-human body or inanimate object).

The target electrode 12 paired with the return electrode 16 defines a monopolar channel and the target electrode 14 paired with the return electrode 16 defines another monopolar channel that share a common ground. In addition, energizing of both target electrodes 12 and 14 creates a bipolar mode of energy delivery.

The voltage waveform applied to each target electrode 12 or 14 gives rise to a respective electrical field component in the tissue. Current flow is determined by the combination of the two components. A voltage difference between the target electrodes 12 and 14 produces substantially Joule heating in a bipolar mode; in contrast, a common voltage at the target electrodes 12, 14 relative to the return electrode 16 substantially produces Joule heating in a monopolar mode. It is noted that the distance between target electrodes 12 and 14 may be small compared to the spacing between the target electrodes 12, 14 and the common return electrode 16. Electrical field components respectively associated with opposing voltage waveforms at the target electrodes 12, 14 virtually cancel each other at distances significantly larger than the inter-electrodes spacing. Joule heating is then confined to a volume adjacent to the target electrodes 12 and 14 in a fashion substantially equivalent to bipolar mode heating.

Figure 2:
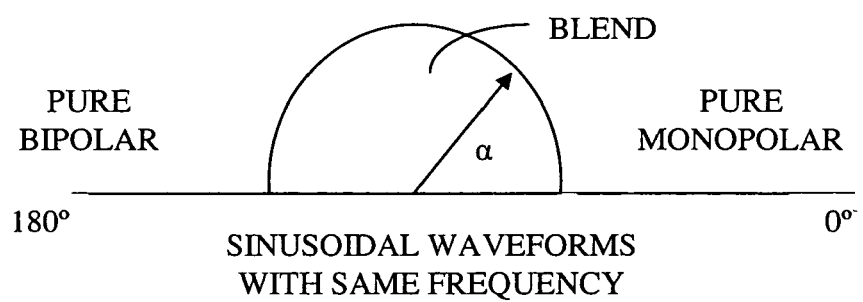
FIG. 2 is a simplified graphical illustration of modes of operation (monopolar, bipolar, blend of both) when voltage waveforms are sinusoidal with the same frequency, in accordance with an embodiment of the present invention.

Reference is now made to FIG. 2, which graphically illustrates the situation when the voltage waveforms are sinusoidal with the same frequency. In this case, the inter-waveforms phase angle α determines the polarity mode. For example, a 0° phase causes a monopolar mode since in this case the individual target electrodes 12 and 14 act as a common target electrode. Similarly, a 180° phase causes a bipolar mode. Phase variation controls the ratio between monopolar and bipolar modes in a combined (blended) mode.

Figure 3:
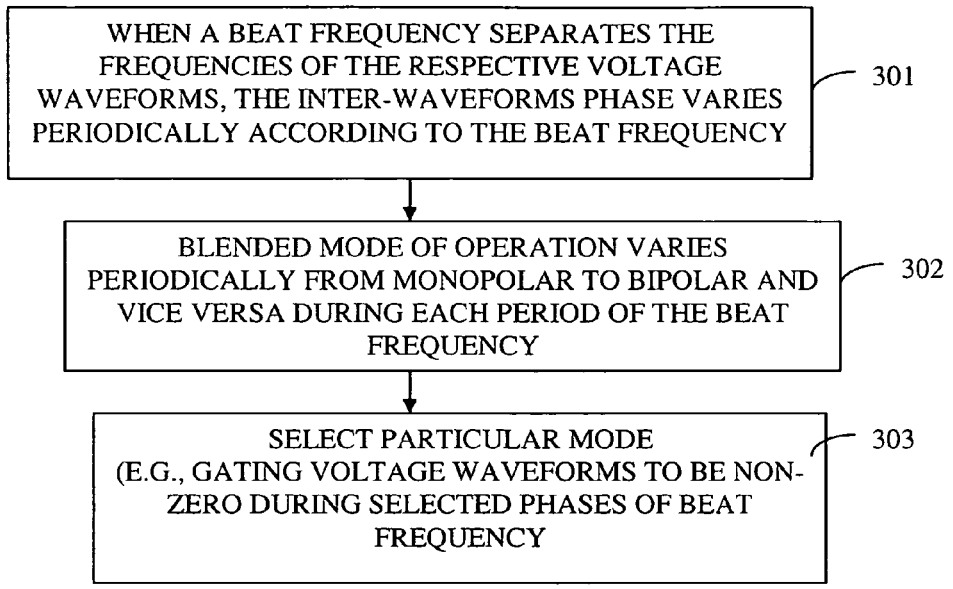
FIG. 3 is a simplified chart of methods of varying the waveforms to blend monopolar and bipolar modes of operation, in accordance with an embodiment of the present invention.
Figure 3:
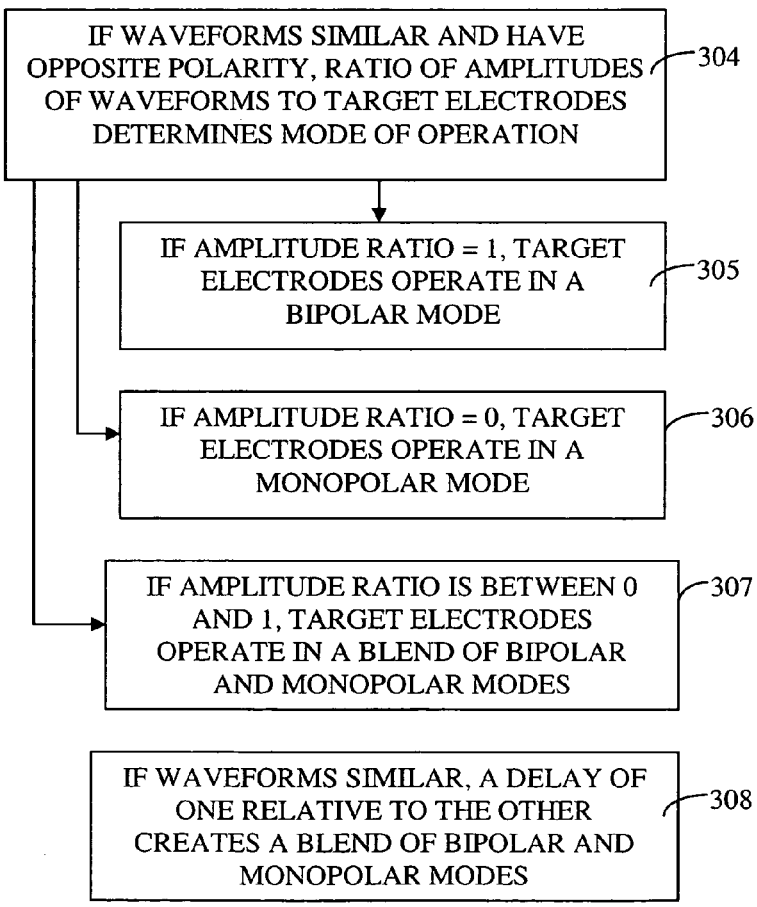

Reference is now made to FIG. 3, which illustrates other methods of varying the waveforms to blend monopolar and bipolar modes of operation. When a beat frequency separates the frequencies of the respective voltage waveforms, the inter-waveforms phase varies periodically according to the beat frequency (301). As a result, the blended mode of operation varies periodically from monopolar to bipolar and vice versa during each period of the beat frequency (302). A particular mode can be selected, for example, by gating the voltage waveforms to be non-zero during selected phases of the beat frequency (303).

When the voltage waveforms are similar and have opposite polarity, the ratio of the amplitudes of the waveforms to the target electrodes 12 and 14 determines the mode of operation (304). If the amplitude ratio=1, the target electrodes 12 and 14 operate in a bipolar mode (305). If the amplitude ratio=0, the target electrodes 12 and 14 operate in a monopolar mode (306). If the amplitude ratio is between 0 and 1, the target electrodes 12 and 14 operate in a blend of bipolar and monopolar modes (307). If the voltage waveforms are similar, a delay of one relative to the other creates a blend of bipolar and monopolar modes (308).

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A system comprising:
at least two target electrodes and at least one return electrode;
at least two RF power sources in electrical communication with said electrodes and operative to generate RF energy waveforms to said at least two target electrodes, one of said at least two target electrodes cooperating with said at least one return electrode to define a monopolar RF energy delivery channel and another of said at least two target electrodes cooperating with said at least one return electrode to define another monopolar RF energy delivery channel, said at least one return electrode being common to both channels, wherein said at least two target electrodes being operable in a bipolar mode of RF energy delivery; and
a waveform manipulator operable to control and manipulate the waveforms to said at least two target electrodes so as to selectively provide pure monopolar, pure bipolar and a blend of monopolar and bipolar modes of RF energy delivery, wherein said waveforms are sinusoidal with respective frequencies separated by a beat frequency, and said waveform manipulator is operative to modulate said waveforms according to a phase of the beat frequency.

2. The system according to claim 1, wherein a distance between said at least two target electrodes is smaller than a spacing between said at least two target electrodes and said common return electrode.

3. The system according to claim 1, wherein said waveform manipulator is operative to modulate said waveforms by gating the waveforms to be non-zero during selected phases of the beat frequency.

4. A method comprising:
providing at least two target electrodes and at least one return electrode;
providing at least two RF power sources in electrical communication with said electrodes and operative to generate RF energy waveforms to said at least two target electrodes, one of said at least two target electrodes cooperating with said at least one return electrode to define a monopolar RF energy delivery channel and another of said at least two target electrodes cooperating with said at least one return electrode to define another monopolar RF energy delivery channel, said at least one return electrode being common to both channels, wherein said at least two target electrodes being operable in a bipolar mode of RF energy delivery; wherein a distance between said at least two target electrodes is smaller than a spacing between said at least two target electrodes and said common return electrode;
controlling and manipulating the waveforms to said at least two target electrodes so as to selectively provide pure monopolar, pure bipolar and a blend of monopolar and bipolar modes of RF energy delivery, wherein said waveforms are sinusoidal with respective frequencies separated by a beat frequency, and said waveforms are modulated according to a phase of the beat frequency.

5. The method according to claim 4, wherein modulating said waveforms comprises gating the waveforms to be non-zero during selected phases of the beat frequency.

* * * * *